United States Patent [19]

Pascoe et al.

[11] Patent Number: 4,749,525
[45] Date of Patent: Jun. 7, 1988

[54] PROCESS FOR THE CARBONYLATION OF PROPYLENE

[75] Inventors: Ralph F. Pascoe, Marysville; Carlo Scaccia, Worthington, both of Ohio

[73] Assignee: Ashland Oil, Inc., Ashland, Ky.

[21] Appl. No.: 881,425

[22] Filed: Jul. 2, 1986

[51] Int. Cl.$^4$ .............................................. C07C 51/58
[52] U.S. Cl. .............................. 260/544 A; 260/544 F
[58] Field of Search ........................ 260/544 A, 544 F

[56] References Cited

U.S. PATENT DOCUMENTS

| | | | |
|---|---|---|---|
| 4,451,670 | 5/1984 | Grote et al. | 260/544 A |
| 4,499,029 | 2/1985 | Scaccia et al. | 260/544 A |
| 4,504,675 | 3/1985 | Besecke et al. | 562/521 |
| 4,590,293 | 5/1986 | Pascoe | 562/521 |
| 4,661,296 | 4/1987 | Grote et al. | 562/521 |

OTHER PUBLICATIONS

Rohm GMBH, *Derwent Abstract*, 53612 D/30, (E.P.A. 0,031,886, Laid Open Jul. 15,1981).
Rohm GMBH, *Derwent Abstract*, 83-789, 751/42, (German 3,213,395, A1 Laid Open Oct. '83).

*Primary Examiner*—Paul J. Killos
*Assistant Examiner*—L. Hendriksen
*Attorney, Agent, or Firm*—John F. Jones

[57] ABSTRACT

A process for the improvement in the utilization of carbon monoxide and for the utilization of propylene having varying grades of purity in the carbonylation of propylene with carbon monoxide and hydrogen fluoride to form isobutyryl fluoride in a carbonylation reactor whereby the effluent from the reactor is (a) passed into a first phase separator where the effluent is separated into an overhead gaseous stream and a bottom liquid stream which contains unreacted carbon monoxide, (b) the bottom liquid stream from (a) is passed into a second reactor where it is contacted with a gaseous stream which contains propylene and allowing essentially all of the propylene to react, (c) the effluent from the second reactor is passed to a second phase separator where overhead gases are separated from liquid bottoms, (d) the liquid bottoms from the second phase separator are passed to a degassing pot where overhead gases are removed and the liquid bottoms stream which is essentially isobutyryl fluoride is taken to recovery, (e) the overhead gases from (d) are optionally mixed with inert gases and the stream is recycled to the hydrogen fluoride fed to the carbonylation reactor and/or recycled back to the gaseous stream in (b), (f) the gases from overhead stream in (a) are passed to a compressor and then to the recycle gaseous stream from (e), (g) the overhead gases from (e) are divided into a first portion which is sent to recycle as in (e) and a second portion which is sent to a refrigeration unit where said second portion into a bottom stream of less volatile materials and an overhead stream of volatile materials, a portion of the bottoms stream is added to the isobutyryl fluoride stream for recovery in (d), and the overhead, less volatile stream from (g) is sent to waste disposal is described.

2 Claims, 1 Drawing Sheet

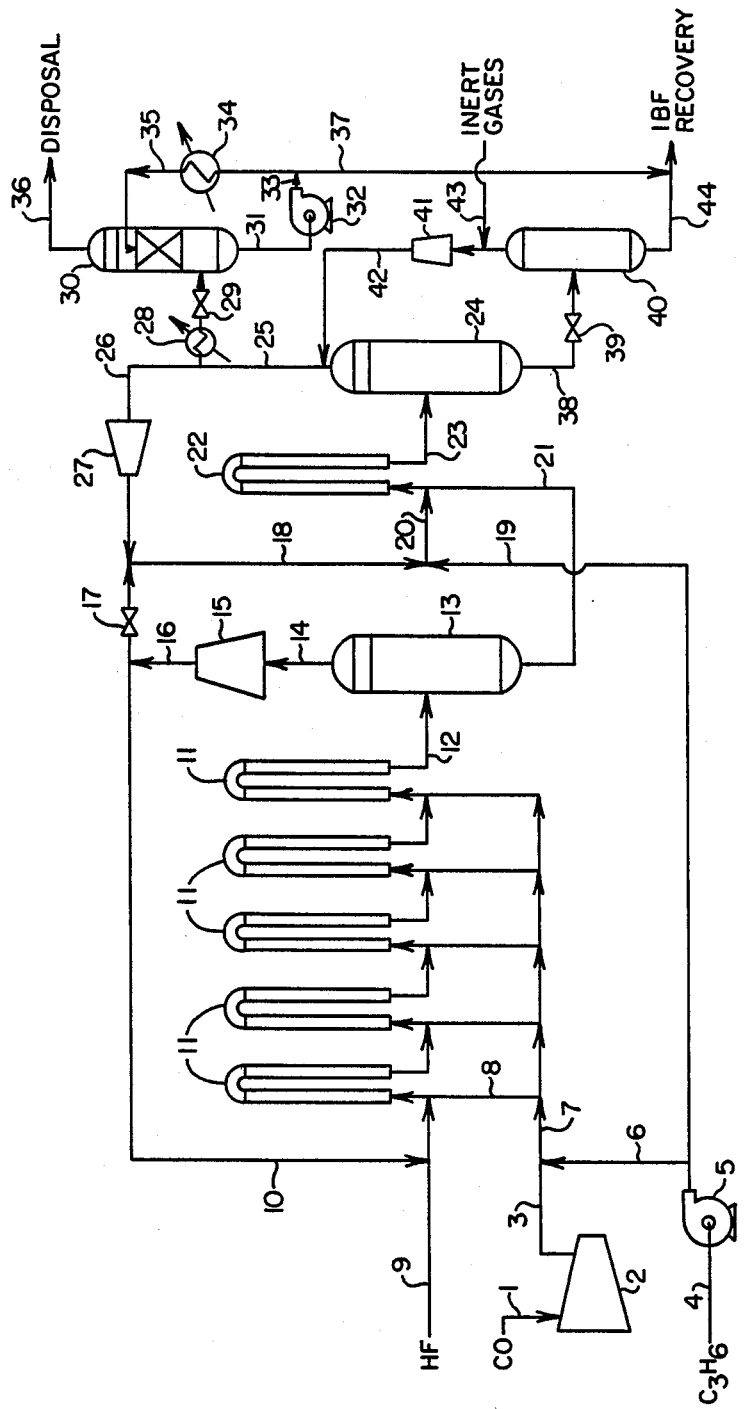

PROCESS FOR THE CARBONYLATION OF PROPYLENE

This invention relates to an improved process for the carbonylation of propylene with carbon monoxide in the presence of hydrogen fluoride to form isobutyryl fluoride which improvement insures the optimal utilization of the carbon monoxide.

The production of isobutyric acid and isobutyryl fluoride by the Koch reaction is well known to those skilled in the art. In the U.S. patent No. 4,499,029 an improved process for the production of isobutyryl fluoride is described wherein propylene, carbon monoxide and hydrogen fluoride are allowed to react in a continuous flow type of reactor and wherein there is multi-injection within the reactor or between reactors of additional propylene and carbon monoxide. This invention represents an improvement over the process described in U.S. Pat. No. 4,499,029.

Prior art processes for the formation of isobutyryl fluoride by the Koch process have shown various yields and conversions and in many cases high conversions of product have been said to result based on the consumption of propylene. In most, if not all, of the prior art disclosures the yields and conversions to product based on the consumption of carbon monoxide have been very poor. See U.S. Pat. No. 4,452,999, for instance, col. 4, lines 33-36, etc. Unreacted carbon monxide has been considered to be expendable and has been usually discarded with waste gases. The present invention utilizes the carbon monoxide to the fullest extent in view of its value and thus reduces the cost of production of isobutyryl fluoride significantly.

Moreover, the present invention provides a process for fully utilizing both propylene and carbon monoxide even in the case in which the propylene used is not pure and contains extraneous gases. Pure propylene is always more expensive than lower grade propylene mixtures which are often available from petroleum refineries. Lower grade propylene fractions also may contain gases for the most part are inert to the Koch reaction such as ethane, ethylene, propane, isobutane, etc. The present invention enables one to run the Koch reaction in an equally satisfactory manner when employing either pure propylene or cheaper propylene mixtures and in either case virtually all of the propylene and particularly the carbon monoxide in the feed is converted to the desired isobutyryl fluoride.

This invention is further illustrated in the accompanying drawing wherein gaseous carbon monoxide (CO) is brought into the process stream at line 1, where the CO is compressed in unit 2 to a pressure ranging from about 500 to 3000 psia, preferentially at a pressure ranging from about 500 to 1000 psia. Both ambient and process temperatures exceed the dew point temperature of usual and customary CO rich gas mixtures encountered in industrial practice, therefore, condensible components at these pressures are usually not encountered. When condensibles are present they can be removed from the CO before it enters this process by known techniques which are not part of this process. Industrial grade CO often contains traces of $N_2$, $H_2$, $CO_2$ and $O_2$. Traces of oxygen which might be present in the CO, for instance, can readily be removed via adsorbers as is well known in the art. The CO used in the process of the present invention preferably is free of oxygen. Propylene ($C_3H_6$) is brought into the process as a liquid via line 4 to a pressurizing pump 5 capable of achieving process pressures as stated above for CO. Ordinarily propylene is in liquid form and moved by pump, but the use of gaseous propylene is within the scope of this invention. As in the case of CO mentioned above, condensibles such as water, etc. can be removed from the propylene before it enters the process stream. Water can be readily removed from propylene by absorbers as is well known in the art by means not shown and not part of the present invention.

A main fraction of pressurized propylene leaving pump 5 is taken as stream 6 where it is combined with pressurized carbon monoxide shown as stream 3 leaving compressor 2. The merging streams are intimately mixed as stream 7, either as two phases or as one depending on the selected temperature, pressure and composition, and preferred as all in the gaseous phase. The object of the mixing in stream 7 is to assure sufficient uniformity in flow so as to permit one or more portions of stream 7 to be removed as represented by stream 8 such that the composition of said portions is effectually the same as that in stream 7.

A dominantly liquid hydrogen fluoride rich stream is prepared as a combination of hydrogen fluoride rich liquids recycled from downstream recovery equipment plus any makeup hydrogen fluoride (HF) required by the process to maintain continuous operation, and shown as stream 9. Pressurization equipment for stream 9 is not shown, but is provided by suitable pumps as is well known in the art. The HF rich liquids in stream 9 may contain impurities arising either as contained in the make-up feed or from the collective composition of the contacted streams in the process.

A dominantly gaseous stream is also recycled from downstream sources, shown as stream 10. The composition of stream 10 is subject to considerable control, and is primarily dependent on the amounts of gaseous impurities allowed in all of the feed streams, the solubility of such impurities in the liquid process stream 21 as shown and described hereinafter, and on the fractional amount of stream 16 selected for recycle as recycle loop through valve 17. Stream 10 may contain greater or lesser amounts of gases such fluoride, hydrogen, helium, neon, propylene, HF and others. Stream 10 will preferentially dominate in CO content, but will ordinarily contain a lesser concentration of CO than is found in stream 1.

Stream 10 is admixed with stream 9 with sufficient intensity to create a well dispersed gaseous/liquid mixture in which the gaseous phase is preferably more continuous than the liquid phase. This well dispersed gas/liquid mixture is then fed concurrently with stream 8 into the inlet of reactor 11. The importance of recycle stream 10 is to provide in conjunction with stream 3, sufficient gas phase dilution of propylene so as to avoid or substantially diminish side reactions in which propylene reacts with other propylene or propylene derivatives to form dimers and higher oligomers of propylene or carbonylated or fluoridated derivatives of propylene.

Reactor 11 is characterized as having one or more stages connected in series such that the effluent from a previous stage becomes a feed stream to the following stage. Reactor 11 is also characterized in that various portions of stream 7 can be divided from stream 7 in the same manner as described for stream 8, so that such can be introduced as co-feeds to various reactor stages. The drawing shows reactor 11 as a plug flow apparatus because of simplicity and low cost, but this is not to be construed as meaning that other reactor configurations cannot be used within the scope of this invention.

The reactor effluent, shown as stream 12, is a combination of all feeds and recycle streams less reactants converted to other products, plus the new products, primarily isobutyryl fluoride, formed in the reactor. Stream 12 usually is a mixture of gases and liquids wherein gases are more than 50 volume percent and often are in the order of 90 volume percent of the mixture, particularly in the case in which a plug flow reactor is used.

The material in stream 12 is fed into a phase separator 13 which can be one of several equipment designs suitable for gas/liquid separations at moderately elevated pressure such as an empty vessel containing screens or other impact demisting devices, or a centrifuge, or the like characterized as having sufficient resolution that stream 21 is substantially free from entrained gases and that stream 14 is dominantly gaseous such that compressor or blower 15 can operate effectively as a pressure booster for recycle flows. Repressurized flow in stream 16 from blower 15 is all recycled to the reactor as stream 10 or alternatively some portion of stream 16 can be divided and removed from the primary gaseous recycle loop via valve 17, so as to provide the means to control the composition of gases in stream 10. Without the implementation of valve 17, the only exit for gaseous impurities is via solution in the liquid fraction leaving phase separator 13. Consequently, omission of valve 17 would require that the sum of all gaseous materials and/or impurities in feeds and recycle streams entering the reactor or forming in the reactor be less than the solubility limit of such impurities in the liquid stream leaving the phase separator after correcting for the partial pressure of reactants especially including CO and propylene. The presence of valve 17 is not to be construed as implying the process is limited to feed concentrations of impurities that exceed the solubility limit. Adjustment of valve 17 permits the use of various purities and qualities of feedstocks that range from very pure to significantly less pure and thus provides a process which has a wide range of flexibility and concurrent economy in this respect.

A portion of pressurized propylene from pump 5 is taken as stream 19, and intimately mixed with a dominantly gaseous recycle stream 18 which is described hereinafter. The intensity of mixing, temperature and pressure are sufficient so as to make the liquid fraction well dispersed in the gas phase and preferentially to vaporize the propylene so as to form a dominantly gaseous stream 20. The main purpose of recycle stream 18 is to provide sufficient dilution and dispersion of propylene stream 19 so as to significantly avoid side reactions wherein propylene reacts with propylene or derivatives of propylene to form dimers and higher oligomers or carbonylated or fluoridated derivatives of propylene dimers and higher oligomers.

Streams 20 and 21 are concurrently fed into reactor 22. Reactor 22 is suitable for sufficient gas/liquid contacting particularly in the case where the volume fraction of gases may be 50% or more. In the process of this invention carbon monoxide can be reacted sufficiently toward extinction that the addition of additional propylene reactant via stream 19 causes the desired carbonylation reaction to consume both the carbon monoxide and propylene to result in concentrations in stream 23 leaving the reactor that are very economic when compared to processes embodying liquid phase carbon monoxide stripping or which do not permit dissolved or entrained carbon monoxide to react to form desired product at all.

The process of this invention significantly improves the yield of product with respect to the carbon monoxide in the feed. Stream 23, the effluent from reactor 22, is fed into phase separator 24 which is equipment suitable for separation of gases and liquids at moderately elevated pressure such as an empty vessel or vessel having screens for impact coalescence of droplets (demisting) or centrifuge or the like. Phase separator 24 is characterized in that (1) the liquid phase is substantially free of gaseous entrainment, (2) backmix of gases and liquids following phase separation is kept to a minimum and (3) sufficient liquid hold-up time is provided to permit reaction of the residual carbon monoxide which is dissolved in the liquid phase.

The means by which such objectives are further implemented and controlled is to recycle a well controlled portion of the substantially gaseous effluent stream 25 from phase separator 24. The recycle portion shown as stream 26 is repressurized in blower or compressor 27 and mixed with the vent gases taken through valve 17 to form stream 18. The concentration of CO required in the liquid phase residing in phase separator 24 will ordinarily be controlled so that it is reacted to near extinction. Such control of CO concentration in the liquid phase is provided by control of the partial pressure of CO in the gas phase leaving the phase separator, stream 25, which is in turn controllable via the fraction of stream 25 which is allowed to exit the recycle loop via cooler 28 and valve 29. The magnitude of flow through valve 29 will be directly related to the total gaseous impurities introduced through the feed streams or produced via reaction within the process in order that stable or steady state operation be attained in continous operation.

Gases venting through valve 29 can contain valuable as well as environmentally hazardous materials including HF, CO, propylene and volatile intermediates. A means is included to limit the loses of such components by introducing them into column 30 wherein the less volatile components are made to condense by contacting up-flowing gases with down-flowing refrigerated liquids. Such refrigerated liquids are obtained by collecting liquids in column 30, removing via stream 31, pump 32, and stream 33. Stream 33 is mostly recycled as stream 35 through refrigerator 34 so as to maintain sufficient liquid inventory. Uncondensed gases leave column 30 as stream 36 which may be further treated for process or environmental purposes. A liquid stream approximately equal in mass to the condensible portion of flow through valve 29 is taken as stream 37, combined with liquid stream 38 from phase separator 24 after depressurizing in valve 39. Stream 38 from phase separator 24 will be saturated with gaseous components only insofar as total inerts brought into reactor 22 and vessel 24 exceeds the solubility limit of the liquid stream.

Flow through valve 29 can only exist on a sustained basis when such excess also exists on a sustained basis. Therefore, when raw material feeds are very high purity, the feed through valve 17 is not sufficient to maintain gas recycle stream 25 in both quantity and composition which favors CO reaction to near extinction. For the special case when all raw material feeds are very high purity, then optional means can be implemented either singly or in any combination such as to sustain stream 25 flows, as follows:

(a) Depressurize stream 38 in valve 39, and phase separate envolved gases in degassing pot, 40. Such gases can be recompressed in compressor 41 and recycled via stream 42.

(b) Gases collected from downstream equipment may contain allowable inert components suitable for recycle, shown as stream 43. The presence of absence of degassing pot, 40 is not to be construed as a limitation of this invention in as much as down stream equipment such as distillation columns can also be effective as means to degas liquid streams wherein the gaseous portion can be recycled.

(c) Inert gases from usual and customary sources can be introduced for recycle purposes, also shown as stream 43. Stream 44 contains HF and product isobutyryl fluoride (IBF) which goes to a recovery unit not shown. It is the express purpose of these teachings to provide an efficient and economical means to carry out in commercial practice use of wide ranges in purity of raw material feeds and more complete use of CO feedstock; either singly or both without the undesirable consequence of discarding useful intermediates. The combined impurities in raw material feeds which are less than needed for liquid saturation according to the present invention are not counterproductive to higher CO utilization.

We claim:

1. In a process in which propylene, carbon monoxide and hydrogen fluoride are fed to a first carbonylation reactor to produce a gas/liquid effluent containing isobutyryl fluoride, the improvement in utilization of carbon monoxide and the utilization of propylene having varying degrees of purity comprising:

(A) passing said effluent into a first phase separator and separating the effluent into an overhead gaseous stream and a bottom liquid stream which contains unreacted carbon monoxide, (B) passing the bottom liquid stream from (A) into a second reactor where it is contacted with a gaseous stream which contains propylene and allowing essentially all of the carbon monoxide to react, (C) passing the effluent from the second reactor in (B) to a second phase separator where overhead gases are separated from liquid bottoms, (D) removing the liquid bottoms stream from the second phase separator (C) and passing this stream to a degassing pot where overhead gases are removed and a liquid bottoms stream which is essentially isobutyryl fluoride is taken to recovery, (E) taking the overhead gaseous stream from (D) and adding makeup inert gases to it if desired and then recycling this stream to the hydrogen fluoride fed to the first reactor and/or recycling this stream back to the gaseous stream in (B), (F) passing the overhead gaseous stream from (A) to a compressor and then to the recycle gaseous stream from (E), (G) taking the overhead gases from (C) and passing a first portion to recycle as in (E) and a second portion to a refrigeration unit, separating said second portion into a bottom stream of less volatile materials and an overhead stream of volatile materials, adding a portion of the bottoms stream to the isobutyryl fluoride stream for recovery in (D), and (H) taking the overhead less volatile material stream from (G) to waste disposal.

2. The process of claim 1 wherein the gas/liquid effluent used in (A) is a mixture of from 50 to 90% by volume of gases.

* * * * *